(12) United States Patent
Gilgenbach et al.

(10) Patent No.: US 8,940,116 B2
(45) Date of Patent: Jan. 27, 2015

(54) PROCESS FOR MAKING DISPOSABLE ABSORBENT GARMENTS TO REDUCE ABSORBENT BUNCHING

(75) Inventors: Eric-John Raoul Gilgenbach, Winneconne, WI (US); Sara Jane Wille Stabelfeldt, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 646 days.

(21) Appl. No.: 12/649,923

(22) Filed: Dec. 30, 2009

(65) Prior Publication Data
US 2011/0155301 A1 Jun. 30, 2011

(51) Int. Cl.
*A61F 13/15* (2006.01)

(52) U.S. Cl.
CPC ..... *A61F 13/15804* (2013.01); *A61F 13/15593* (2013.01); *A61F 13/15699* (2013.01); *B32B 2305/20* (2013.01); *B32B 2555/02* (2013.01)
USPC ............................ 156/163; 156/164; 156/229

(58) Field of Classification Search
USPC .......................... 156/160, 161, 163, 164, 229
See application file for complete search history.

(56) References Cited

U.S. PATENT DOCUMENTS

| | | | |
|---|---|---|---|
| 4,050,462 A | 9/1977 | Woon et al. | |
| 4,261,782 A * | 4/1981 | Teed | 156/361 |
| 4,300,967 A | 11/1981 | Sigl | |
| 4,309,236 A | 1/1982 | Teed | |
| 4,450,026 A | 5/1984 | Pieniak et al. | |
| 4,486,192 A | 12/1984 | Sigl | |
| 4,655,760 A | 4/1987 | Morman et al. | |
| 4,701,171 A | 10/1987 | Boland et al. | |
| 4,726,807 A | 2/1988 | Young et al. | |
| 4,756,709 A | 7/1988 | Stevens | |
| 5,143,679 A | 9/1992 | Weber et al. | |
| 5,156,793 A | 10/1992 | Buell et al. | |
| 5,376,198 A | 12/1994 | Fahrenkrug et al. | |
| 5,447,462 A | 9/1995 | Smith et al. | |
| 5,531,729 A | 7/1996 | Coles et al. | |
| 5,569,232 A | 10/1996 | Roe et al. | |
| 5,622,581 A | 4/1997 | Ducker et al. | |
| 5,807,368 A | 9/1998 | Helmer | |
| 5,846,232 A | 12/1998 | Serbiak et al. | |
| 5,879,500 A * | 3/1999 | Herrin et al. | 156/204 |
| 5,916,203 A | 6/1999 | Brandon et al. | |
| 5,928,211 A | 7/1999 | Gustafsson et al. | |
| 5,938,651 A | 8/1999 | Widlund et al. | |

(Continued)

FOREIGN PATENT DOCUMENTS

| | | |
|---|---|---|
| CA | 2165486 A1 | 6/1996 |
| EP | 0 321 985 A2 | 6/1989 |

(Continued)

*Primary Examiner* — Jeff Aftergut
(74) *Attorney, Agent, or Firm* — Kimberly-Clark Worldwide, Inc.

(57) ABSTRACT

A process for manufacturing elastomeric disposable absorbent garments having reducing absorbent assembly bunching. In one embodiment, the process comprises stretching an elastomeric body panel web; thereafter contracting the body panel web to define a contracted portion; and attaching an absorbent assembly to the contracted portion of the body panel web. In another embodiment, the process comprises providing first and second elastomeric body panel webs both in a stretched state; allowing each body panel web to at least partially contract from the stretched state to a contracted state, thereby defining a contracted portion in each body panel web; and attaching an absorbent assembly to the contracted portion of each body panel web.

21 Claims, 6 Drawing Sheets

(56) References Cited

U.S. PATENT DOCUMENTS

| | | | |
|---|---|---|---|
| 5,968,029 A | 10/1999 | Chappell et al. | |
| 6,193,701 B1 | 2/2001 | Van Gompel et al. | |
| 6,231,557 B1 | 5/2001 | Krautkramer et al. | |
| 6,245,401 B1 | 6/2001 | Ying et al. | |
| 6,309,487 B1 | 10/2001 | Herrin et al. | |
| 6,313,372 B1 | 11/2001 | Suzuki | |
| 6,375,646 B1 | 4/2002 | Widlund et al. | |
| 6,465,073 B1 | 10/2002 | Morman et al. | |
| 6,500,377 B1 | 12/2002 | Schneider et al. | |
| 6,562,166 B2 | 5/2003 | Molander et al. | |
| 6,570,056 B1 | 5/2003 | Tanzer et al. | |
| 6,582,413 B2 | 6/2003 | Krautkramer et al. | |
| 6,682,514 B1 | 1/2004 | Brunner | |
| 6,702,800 B1 | 3/2004 | Vukos et al. | |
| 6,706,135 B2 | 3/2004 | Taylor et al. | |
| 6,833,179 B2 | 12/2004 | May et al. | |
| 6,840,928 B2 | 1/2005 | Datta et al. | |
| 6,855,223 B2 | 2/2005 | Johnson | |
| 6,939,334 B2 | 9/2005 | Odorzynski et al. | |
| 6,960,197 B1 | 11/2005 | Gustafsson et al. | |
| 6,974,514 B2 | 12/2005 | Hamulski et al. | |
| 6,979,380 B2 | 12/2005 | Thorson et al. | |
| 7,220,335 B2 | 5/2007 | Van Gompel et al. | |
| 7,252,730 B2 | 8/2007 | Hoffman et al. | |
| 7,294,593 B2 | 11/2007 | Morman et al. | |
| 7,344,523 B2 | 3/2008 | Van Gompel et al. | |
| 7,407,557 B2 | 8/2008 | Wada et al. | |
| 7,419,562 B2 | 9/2008 | Van Gompel et al. | |
| 7,422,991 B2 | 9/2008 | Baldauf et al. | |
| 7,438,779 B2 * | 10/2008 | Nakakado | 156/164 |
| 7,604,624 B2 | 10/2009 | Veith et al. | |
| 2002/0022817 A1 | 2/2002 | Ishikawa | |
| 2004/0064121 A1 | 4/2004 | Van Gompel et al. | |
| 2004/0116887 A1 | 6/2004 | Thorson et al. | |
| 2005/0124948 A1 | 6/2005 | Morman et al. | |
| 2005/0124961 A1 | 6/2005 | Morman et al. | |
| 2005/0143710 A1 | 6/2005 | Van Gompel et al. | |
| 2005/0215972 A1 | 9/2005 | Roe et al. | |
| 2005/0256489 A1 | 11/2005 | Sawyer et al. | |
| 2005/0275148 A1 | 12/2005 | Beaudoin et al. | |
| 2006/0111686 A1 | 5/2006 | Schneider | |
| 2006/0224137 A1 | 10/2006 | McCabe et al. | |
| 2006/0259003 A1 | 11/2006 | Venkitaraman et al. | |
| 2006/0292328 A1 | 12/2006 | Baldauf et al. | |
| 2007/0101476 A1 | 5/2007 | Van Gompel et al. | |
| 2007/0125492 A1 | 6/2007 | Venkitaraman et al. | |
| 2007/0142812 A1 | 6/2007 | Popp et al. | |
| 2007/0202767 A1 | 8/2007 | Anderson et al. | |
| 2007/0208317 A1 | 9/2007 | Krautkramer et al. | |
| 2007/0233034 A1 | 10/2007 | Hildeberg et al. | |
| 2007/0239131 A1 | 10/2007 | Hermansson et al. | |
| 2007/0249254 A1 | 10/2007 | Mansfield | |
| 2007/0293111 A1 | 12/2007 | Mansfield | |
| 2008/0003910 A1 | 1/2008 | Hughes et al. | |
| 2008/0033387 A1 | 2/2008 | Wastlund-Karlsson et al. | |
| 2008/0119102 A1 | 5/2008 | Hughes et al. | |
| 2008/0207071 A1 | 8/2008 | Muslet et al. | |

FOREIGN PATENT DOCUMENTS

| | | | |
|---|---|---|---|
| EP | 0685586 A2 * | 12/1995 | |
| EP | 0 994 686 B1 | 11/2002 | |
| EP | 1 528 133 A1 | 5/2005 | |
| WO | WO 95/12488 | 5/1995 | |
| WO | WO 98/04224 | 2/1998 | |
| WO | WO 00/38918 | 7/2000 | |
| WO | WO 01/43968 | 6/2001 | |
| WO | WO 03/070140 | 8/2003 | |
| WO | WO 2005/122984 | 12/2005 | |
| WO | WO 2006/036090 | 4/2006 | |
| WO | WO 2007/133127 | 11/2007 | |
| WO | WO 2007/133146 | 11/2007 | |
| WO | WO 2008/004138 | 1/2008 | |
| WO | WO 2008/033903 | 3/2008 | |
| WO | WO 2008/060194 | 5/2008 | |
| WO | WO 2008/060204 | 5/2008 | |
| WO | WO 2008/060205 | 5/2008 | |
| WO | WO 2008/079061 | 7/2008 | |

* cited by examiner

PROCESS FOR MAKING DISPOSABLE ABSORBENT GARMENTS TO REDUCE ABSORBENT BUNCHING

BACKGROUND

People rely on disposable absorbent products in their everyday lives, including such articles as adult incontinence products, enuresis pants, training pants, and diapers. Many manufacturers seek to better meet the needs of users of such products. For example, there is a need to further improve fit, discretion, and leakage protection for many products.

Some products employ elasticization across the front and/or back of the garment to assist in keeping the product fit snugly against the wearer. Some products employ a multiplicity of elastic strands within front and/or back waist panels to provide the elasticization, while other products employ elastomeric polymeric films, often sandwiched with one or more nonwoven layers. Most products also include an absorbent member, constructed from wood pulp fluff, superabsorbent polymers, or other absorbent material to absorb fluids such as urine. The absorbent member is typically positioned in the crotch region and extends forward and backward into the front and/or back regions of the product. In certain prior art products, some of the elastic members that extend across the front and/or back waist panels overlap the absorbent member at various locations, by virtue of the absorbent member extending forward/backward into the front/back waist regions. This can be undesirable, because the tension of the elastic members can tend to gather the absorbent member, or cause it to "bunch." Such bunching of the absorbent member can create fit and discretion problems. From a fit standpoint, a bunched absorbent is less likely to lie snugly against the body, potentially increasing the incidence of leakage. From a discretion standpoint, excessive bunching tends to make the product more bulky and therefore more visible under clothing. This circumstance is particularly problematic for incontinence articles, such as enuresis pants and adult pull-on style disposable absorbent underwear, as the wearers of such products generally are embarrassed about their condition and wish to employ protection which is as discreet as possible.

In certain conventional processes to manufacture disposable absorbent pants having elasticization, an absorbent composite (such as a pulp fluff/superabsorbent matt sandwiched between polymeric film and/or nonwoven layers) is affixed to one or more elastomeric panels designed to form part of the pant and to fit snugly against the body. These elastomeric panels are provided in continuous web form and are unrolled into the manufacture process in a stretched state. Each absorbent composite is attached to the continuous web of elastomeric material in such stretched state. Upon completion of the manufacturing steps (after the absorbent composite has been attached), the elastomeric material is allowed to contract. This contraction can cause the absorbent composite to bunch and gather, which is undesirable as explained above.

Therefore, there remains a need for a process for producing absorbent garments having elasticized panels that are less likely to cause undesirable gathering and bunching of the absorbent member.

SUMMARY OF THE INVENTION

In response to the above described unmet needs in the art, a new process for manufacturing elastomeric disposable absorbent garments has been invented. In one embodiment, the process comprises stretching an elastomeric body panel web; thereafter contracting the body panel web to define a contracted portion; and attaching an absorbent assembly to the contracted portion of the body panel web. The process can comprise thereafter restretching at least a portion of the contracted portion of the body panel web. In particular embodiments, the body panel web comprises an elastomeric film laminate in which an elastomeric film layer is sandwiched between opposing nonwoven layers.

In particular embodiments of the process, contracting the body panel web comprises slowing the speed of the body panel web by temporarily securing the body panel web to a first variable-speed member, such as via vacuum force. In certain embodiments, the process further comprises securing the body panel web to the first variable-speed member and to a second variable-speed member spaced from the first variable-speed member; moving the first variable-speed member closer to the second variable-speed member, such that the body panel web contracts in a region between the first and second variable-speed members to define the contracted portion. After attaching the absorbent assembly to the contracted portion, such embodiment further comprises moving the first variable-speed member away from the second variable-speed member; and subsequently releasing the body panel web from the first and second variable-speed members. In one version, the variable-speed members move in orbital motion about an axis.

In another embodiment of the process, contracting the body panel web comprises slowing the speed of the body panel web using a reduced-speed paired-roller nip. One embodiment further comprises feeding the body panel web sequentially through a first paired-roller nip, a second paired-roller nip, a third paired-roller nip, and a fourth paired-roller nip, wherein the both the second paired-roller nip and the third paired-roller nip draw more slowly than the first paired-roller nip, wherein the absorbent assembly is attached to the body panel web between the second paired-roller nip and the third paired-roller nip, and wherein the fourth paired-roller nip draws more quickly than the third paired-roller nip. Another embodiment comprises passing the body panel web through a first paired-roller nip; passing the body panel web through a second paired-roller nip downstream of the first paired-roller nip, the second paired-roller nip having a slower draw than the first paired-roller nip; passing the body panel web through a third paired-roller nip downstream of the second paired-roller nip, the third paired-roller nip having a draw speed substantially equal to the draw speed of the second paired-roller nip; passing the body panel web through a fourth paired-roller nip downstream of the third paired-roller nip, the fourth paired-roller nip having a faster draw than the third paired-roller nip; and attaching the absorbent assembly to the body panel web between the second paired-roller nip and the third paired-roller nip.

In another embodiment, the process comprises providing first and second elastomeric body panel webs both in a stretched state; allowing each body panel web to at least partially contract from the stretched state to a contracted state, thereby defining a contracted portion in each body panel web; and attaching an absorbent assembly to the contracted portion of each body panel web. In particular embodiments, the process further comprises restretching at least a portion of the contracted portion of the first body panel web and/or of the second body panel web. In particular embodiments, each body panel web comprises an elastomeric film laminate in which an elastomeric film layer is sandwiched between opposing nonwoven layers.

In particular embodiments, contracting the first body panel web comprises slowing the speed of the first body panel web by temporarily securing the first body panel web to a first variable-speed member, and contracting the second body panel web comprises slowing the speed of the second body panel web by temporarily securing the second body panel web to a third variable-speed member. In certain embodiments, temporarily securing the body panel webs to the first and third variable-speed members occurs via vacuum force. Certain embodiments further include securing the first body panel web to the first variable-speed member and to a second variable-speed member spaced from the first variable-speed member; moving the first variable-speed member closer to the second variable-speed member, such that the first body panel web contracts in a region between the first and second variable-speed members to define the contracted portion in the first body panel web; after attaching the absorbent assembly to the contracted portion in the first body panel web, moving the first variable-speed member away from the second variable-speed member; and releasing the first body panel web from the first and second variable-speed members. Such embodiments of the process can further comprise securing the second body panel web to the third variable-speed member and to a fourth variable-speed member spaced from the third variable-speed member; moving the third variable-speed member closer to the fourth variable-speed member, such that the second body panel web contracts in a region between the third and fourth variable-speed members to define the contracted portion in the second body panel web; after attaching the absorbent assembly to the contracted portion in the second body panel web, moving the third variable-speed member away from the fourth variable-speed member; and releasing the second body panel web from the third and fourth variable-speed members. In a particular version of the embodiment just described, the first variable-speed member is integral with the third variable-speed member, and the second variable-speed member is integral with the fourth variable-speed member.

In another version of the process embodiment being described which employs first and second elastomeric body panel webs, contracting each body panel web comprises slowing the speed of each body panel web using a reduced-speed paired-roller nip. Certain embodiments of this version further comprises feeding each body panel web sequentially through a first paired-roller nip, a second paired-roller nip, a third paired-roller nip, and a fourth paired-roller nip, wherein both the second paired-roller nip and the third paired-roller nip draw more slowly than the respective first paired-roller nip, wherein the absorbent assembly is attached to each body panel web between the respective second paired-roller nip and the respective third paired-roller nip, and wherein each fourth paired-roller nip draws more quickly than the respective third paired-roller nip. In certain embodiments, the process further comprises passing each body panel web through a first paired-roller nip; passing each body panel web through a second paired-roller nip downstream of the first paired-roller nip, the second paired-roller nip having a slower draw than the first paired-roller nip; passing each body panel web through a third paired-roller nip downstream of the second paired-roller nip, the third paired-roller nip having a draw speed substantially equal to the draw speed of the second paired-roller nip; passing each body panel web through a fourth paired-roller nip downstream of the third paired-roller nip, the fourth paired-roller nip having a faster draw than the third paired-roller nip; and attaching the absorbent assembly to each body panel web between the second paired-roller nip and the third paired-roller nip. In one example of such an embodiment, the first body panel web passes through a first set of first, second, third, and fourth paired-roller nips, and wherein the second body panel web passes through a second set of first, second, third, and fourth paired-roller nips physically distinct from the first set.

In still another embodiment, the manufacturing process of the present invention comprising the steps of: providing an elastomeric film laminate body panel web traveling at a first production speed; slowing the travel of the body panel web to an application speed; providing an absorbent assembly traveling at the application speed; attaching the absorbent assembly to the body panel web at the application speed; and accelerating the travel of the body panel web to a second production speed after the absorbent assembly has been attached to the body panel web. In one version, the second production speed is between 70 and 95 percent of the first production speed.

By using the above techniques, elastomeric panels in finished garments (such as front body panel or back body panels) will in certain embodiments impart relatively reduced gathering/contracting force upon the absorbent assembly, thus reducing or eliminating unsightly bunching.

DETAILED DESCRIPTION OF PARTICULAR EMBODIMENTS

Figure 1:
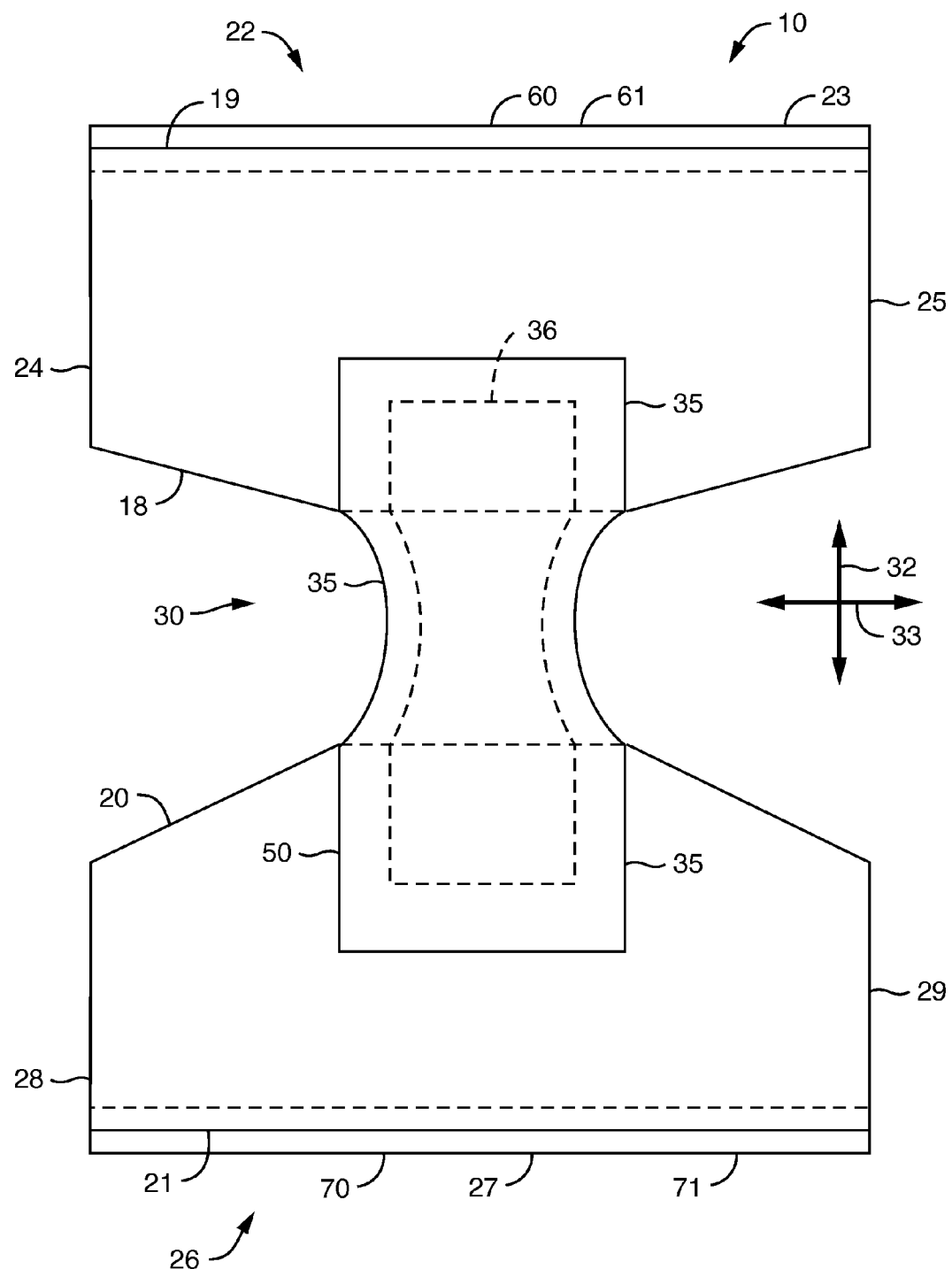
FIG. 1 representatively illustrates a plan view of one embodiment of an absorbent garment incorporating the principles of the present invention in a longitudinally stretched and laid-flat condition, prior to the joining of the front and back waist regions, and showing the surface of the article that faces the wearer when the article is worn.
Figure 2:
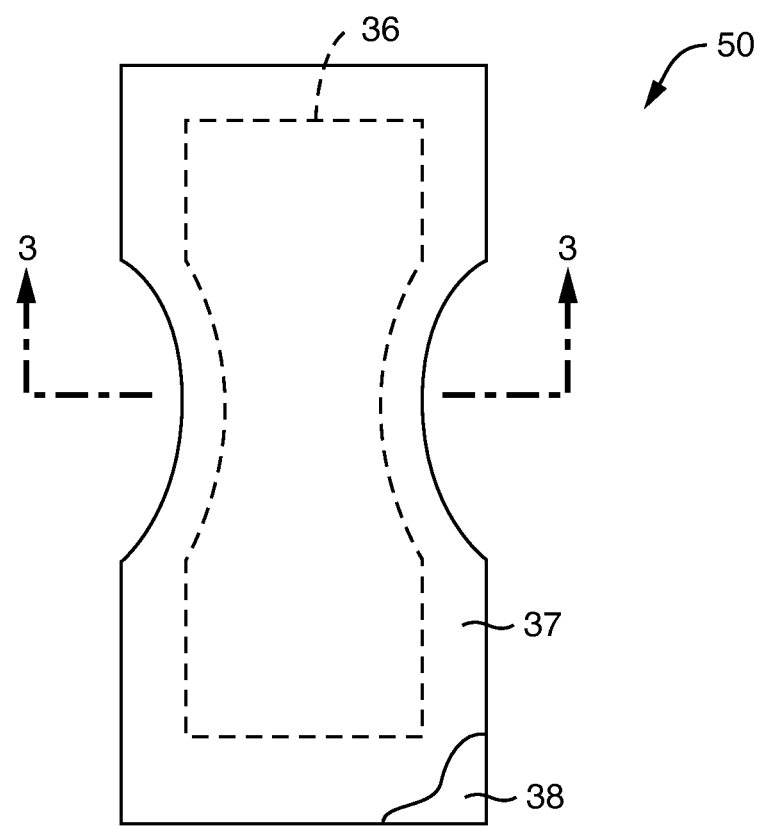
FIG. 2 representatively illustrates a plan view of an absorbent assembly suitable for use in conjunction with the present invention, showing the surface of the absorbent assembly would face the wearer, and shown with portions cut away to show underlying features.
Figure 3:
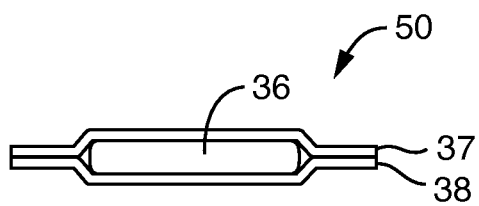
FIG. 3 representatively illustrates a cross-sectional view taken along line 3-3 in FIG. 2.

As used herein, the following terms have the following meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastomeric" refers to a material or composite which can be elongated by at least 50 percent of its relaxed length and which will recover, upon release of the applied force, at least 50 percent of its elongation. It is generally preferred that the elastomeric material or composite be capable of being elongated by at least 100 percent, more preferably by at least 200 percent, of its relaxed length and recover, upon release of an applied force, at least 50 percent of its elongation. "Non-elastomeric" refers to a material or composite that is non-extensible, or that is extensible but will recover no more than 20 percent of its elongated length after release of an applied elongating force. "Non-extensible" refers to a material that cannot stretch or extend by more than 25 percent of its relaxed length without fracture upon application of a biasing force.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

These terms may be defined with additional language elsewhere in the specification.

Reference to FIGS. 1 to 7 shall be made in describing various aspects and embodiments of the invention. It should be noted that the embodiments depicted the Figures are merely representative examples of the principles of the invention. Although for illustrative purposes certain features of the present invention shall be described and illustrated with respect to a process for producing a pull-on pant-style incontinence or enuresis garment, the various aspects and embodiments of the present invention are also suitable for use with diapers, swim pants, training pants, and the like.

Figure 4:
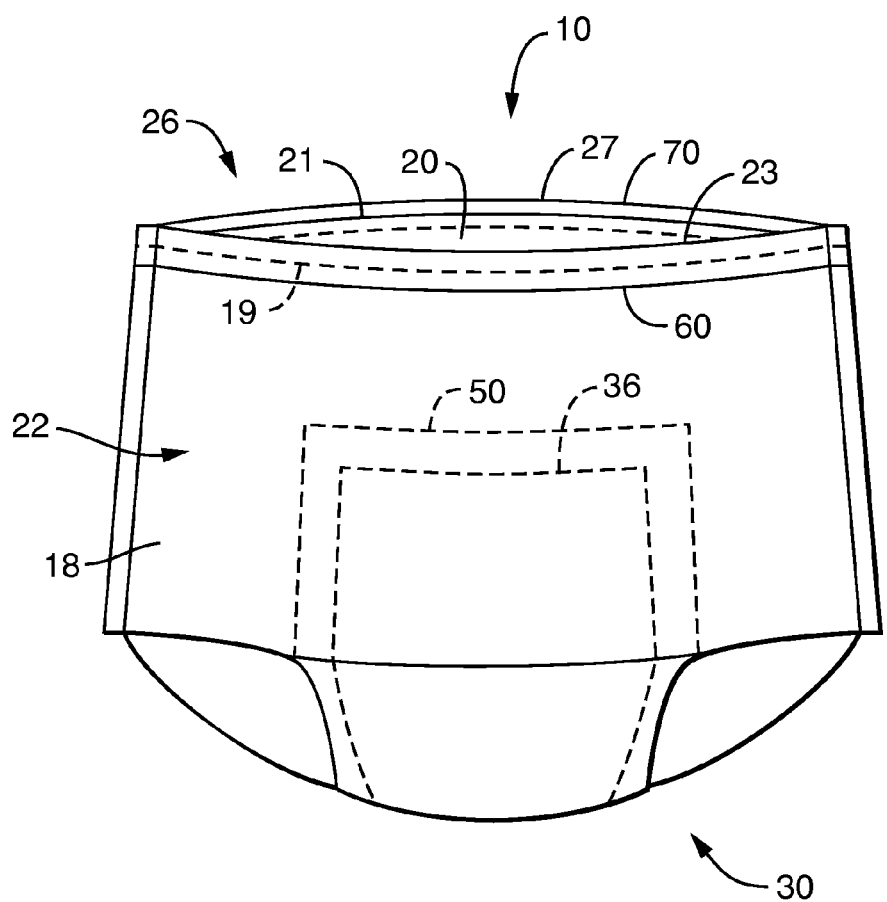
FIG. 4 representatively illustrates a front perspective view of a garment embodiment such as that depicted in FIG. 1, with the front and back waist regions being joined such that the garment is in a pull-on, pant-like configuration.

Referring to FIGS. 1 and 4, a particular embodiment of an absorbent garment 10 of the present invention defines a front region 22 having a front edge 23 and transversely opposed first and second front side edges 24 and 25, a back region 26 having a back edge 27 and transversely opposed first and second back side edges 28 and 29, and a crotch region 30 disposed longitudinally between and which interconnects the front and back regions 22 and 26. The front region comprises a front panel 18 defining a front panel end edge 19, and the back region comprises a back panel 20 defining a back panel end edge 21. The absorbent garment defines a longitudinal direction 32 which extends from the front region 22 to the back region 26, and a transverse direction 33 which is perpendicular to the longitudinal direction 32. It should be noted that the use of the terms "front" and "back," such as with "front region" and "back region" and "front panel" and "back panel" is merely for reference purposes in describing and aiming the garment and process of the present invention, and does not imply that the region or edge align with any particular position on the wearer. Thus, for example, the "front region" of a garment as described herein could be that region of the product that is intended to be positioned on the wearer's front waist, or on the wearer's back waist. Likewise, the "back region" of the garment could be that region of the product that is intended to be positioned on the wearer's front waist, or on the wearer's back waist. The front panel 18 and back panel 20 are constructed of elastomeric materials. In one desirable example, the front and back panels are constructed of an elastomeric film laminate, such as a film laminate comprising an elastomeric film layer sandwiched between two nonwoven facing layers. In an alternative, the front and back panels are constructed of an elastic strand laminate, in which a series of spaced apart elastic strands are sandwiched between two nonwoven facing layers.

The garment includes an absorbent assembly 50 which extends longitudinally from the front region 22 to the back region 26. The absorbent assembly 50 includes an absorbent member 36. The absorbent member can be constructed of materials known in the art as suitable for absorbing liquid excretions, such as wood pulp fluff, superabsorbent polymers, absorbent foam, and the like. The absorbent member is, in particular embodiments, encased in one or more substrates. For example, the absorbent member could be wrapped in a tissue and/or a nonwoven substrate. Alternatively, or in addition, the absorbent member can be sandwiched between a garment-side, liquid impermeable backsheet and a body-side, liquid permeable liner. For example, the absorbent assembly 50 can be constructed of an absorbent member 36 sandwiched between a liner 37 and a backsheet 38, as representatively illustrated in FIGS. 2 and 3.

In particular embodiments, a front elastomeric waistband 60 is attached to the front panel 18, and a back elastomeric waistband 70 is attached to the back panel 20. The longitudinally outermost edge 61 of the front elastomeric waistband 60 can be coterminous with the front panel end edge 19 (not shown). Alternatively, as representatively illustrated in FIGS. 1 and 4, at least part of the front elastomeric waistband 60 can extend longitudinally between the front panel end edge 19 and the front edge 23, such that the waistband 60 is "cantilevered" off the front panel end edge 19. Similarly, the longitudinally outermost edge 71 of the back elastomeric waistband 70 can be coterminous with the back panel end edge 21 (not shown). Alternatively, as representatively illustrated in FIGS. 1 and 4, at least part of the back elastomeric waistband 70 can extend longitudinally between the back panel end edge 21 and the back edge 27, such that the waistband 70 is "cantilevered" off the back panel end edge 21. Such waistbands are preferably but not necessarily elastomeric, and can comprise elastomeric films, elastomeric strands or ribbons, elastomeric foams, or the like.

Figure 5:
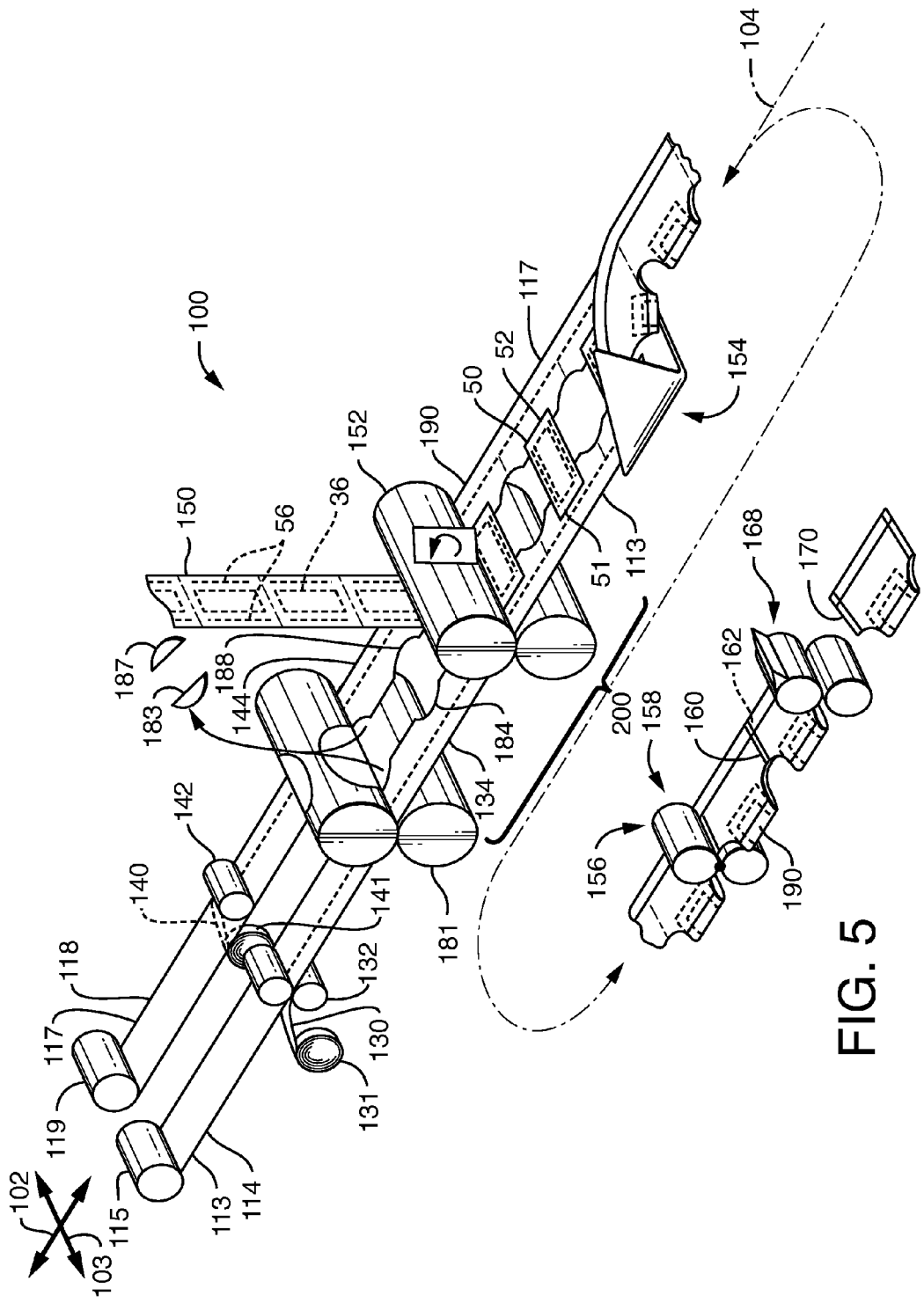
FIG. 5 representatively illustrates a perspective view of a manufacturing process suitable for use in conjunction with certain embodiments.

As representatively illustrated in FIG. 5, the invention in certain aspects relates to a process 100 for manufacturing disposable undergarments. The process defines a machine direction 102 and a cross-machine direction 103. In particular embodiments, the process 100 includes providing a front body panel web 113 traveling in a machine direction 102. The front body panel web 113 defines a front waist edge 114 which extends in the machine direction. The process 100 further comprises providing a back body panel web 117 traveling in the machine direction 102. The back body panel web 117 defines a back waist edge 118 which also extends in the machine direction 102. Preferably, as representatively illustrated in FIG. 5, the front body panel web 113 is distinct from and spaced apart from the back body panel web 117 in the cross-machine direction. In particular embodiments, the front body panel web 113 is provided via a front body panel web supply roll 115, and the back body panel web 117 is provided via a back body panel web supply roll 119. Alternatively, the front and back body panel webs 113/117 may be provided by first providing a "parent" web or roll, and subsequently slitting the parent web along a generally longitudinally extending line, which may be straight or not straight, to provide the front body panel web 113 and the back body panel web 117. The front body panel web and the back body panel web may each comprise a nonwoven material. Each could comprise, for example, an elastomeric film laminate, such as elastic film core layer sandwiched between two nonwoven facing layers, a material which is common to those of skill in the art. U.S. Patent Application Publications US 2008/0095978 and US 2009/0197041, both assigned to Kimberly-Clark Worldwide, Inc., provide examples of technology suitable for use in creating the front and back body panel elastomeric film laminates, although other elastomeric film laminates can also be used.

Still referring to FIG. 5, the process 100 can further include providing a front elastic waistband web 130 and a back elastic waistband web 140, such as via roll supplies 131 and 141 respectively. Such waistband webs can be positioned such that distal edges 134/144 are substantially flush with, laterally outward of, or laterally inward of the respective waist edge 114/118. As depicted in FIG. 5, the waistband webs 130/140 may be distinct and separately provided from and attached to the front and back body panel webs 113/117. Alternatively, the waistband webs 130/140 may be integral with and formed by folding the front and back body panel webs 113/117 (not shown). The process 100 can include attached the waistband webs 130/140 to the front and back body panel webs 113/117 at attachment stations 132/142.

The process 100 can also include removing central portions 183 of the front body panel web 113 and/or removing central portions 187 of the back body panel web 117, such as via cutter unit 181, to define shaped front body panel web leg edges 184 and/or shaped back body panel web leg edges 188.

The process in this alternative configuration further includes providing a supply 150 of individual absorbent assemblies 50, each individual absorbent assembly 50 having a front end 51 and a back end 52. The absorbent assemblies can be configured and provided as described earlier. Leg elastics 56 which run alongside the absorbent member 36 may be optionally included. The process 100 further includes attaching the front end 51 of each individual absorbent assembly 50 to the front body panel web 113 and attaching the back end 52 of each individual absorbent assembly 50 to the back body panel web 117 (such as at cut-and-rotate attachment station 152) to create a composite garment web 190 such that each individual absorbent assembly 50 extends laterally between and interconnects the front body panel web 113 to the back body panel web 117.

The process 100 can further comprise folding the composite garment web 190 (such as at folding station 154) along a longitudinally extending centerline 104 that extends in the machine direction 102, such that the front waist edge 114 is brought into close proximity with the back waist edge 118. The process further includes attaching the front body panel web 113 to the back body panel web 117 (such as at seaming station 156) to create a series of garment side seam bonds 160 spaced apart in the machine direction 102. The process further includes attaching the front elastic waistband web 130 to the back elastic waistband web 140 (such as at seaming station 158) to create a series of waistband side seam bonds 162 spaced apart in the machine direction 102. Finally, the process includes cutting the composite garment web 190 and the elastic waistband webs 130/140 (such as at cutting station 168) at a series of cut locations 170 spaced apart in the machine direction 102 to create the plurality of disposable absorbent garments. The garment side seam bonds 160 and the waistband side seam bonds 162 can be made at the same seaming station (as depicted) or at separate seaming stations. Additionally, either or both of the seaming operations can be performed along with the final cutting operation at a single station, or at separate stations (as depicted).

Figure 6:
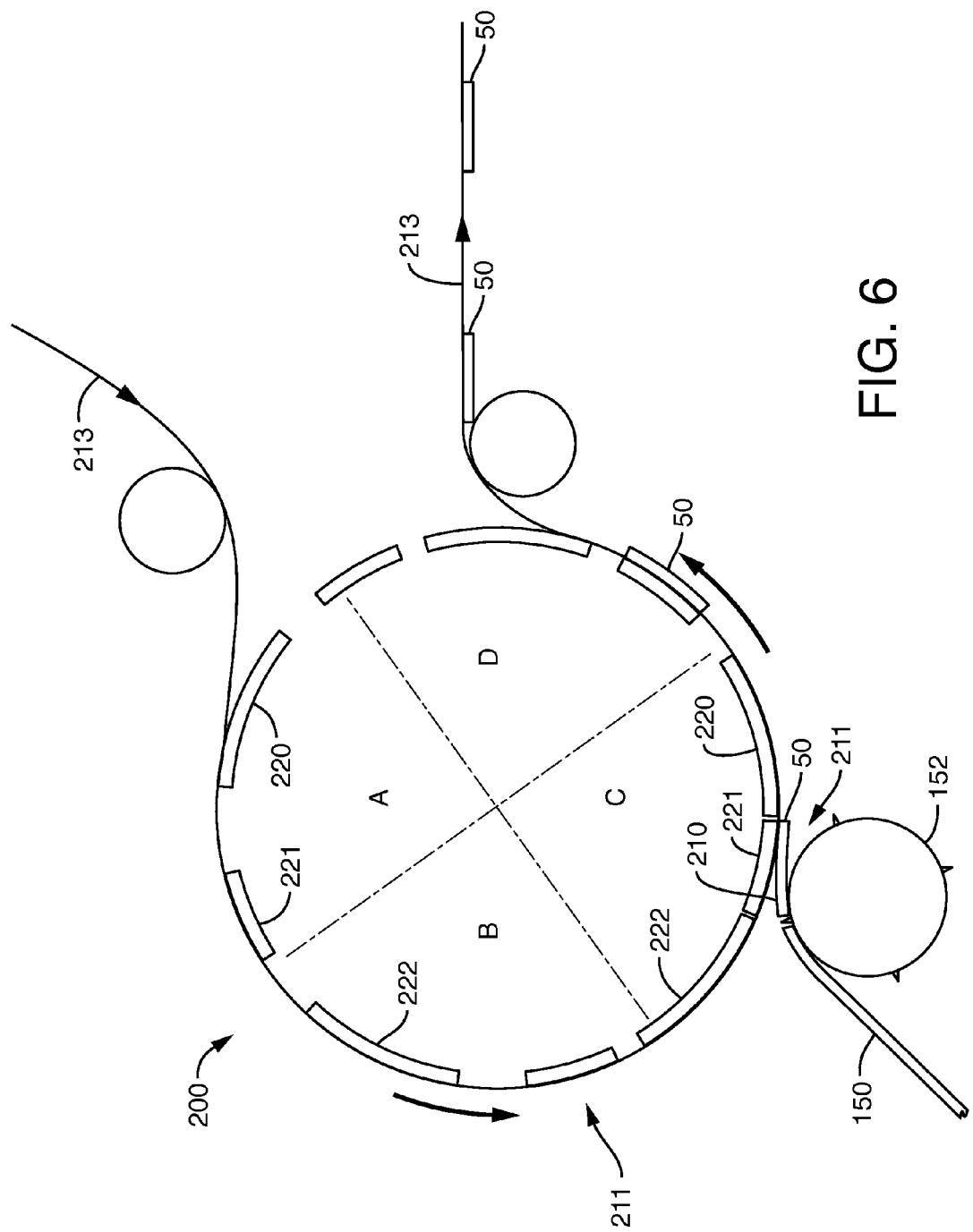
FIG. 6 representatively illustrates a side view of one embodiment of a portion of a garment manufacturing process, the depicted portion incorporating principles of the present invention.
Figure 7:
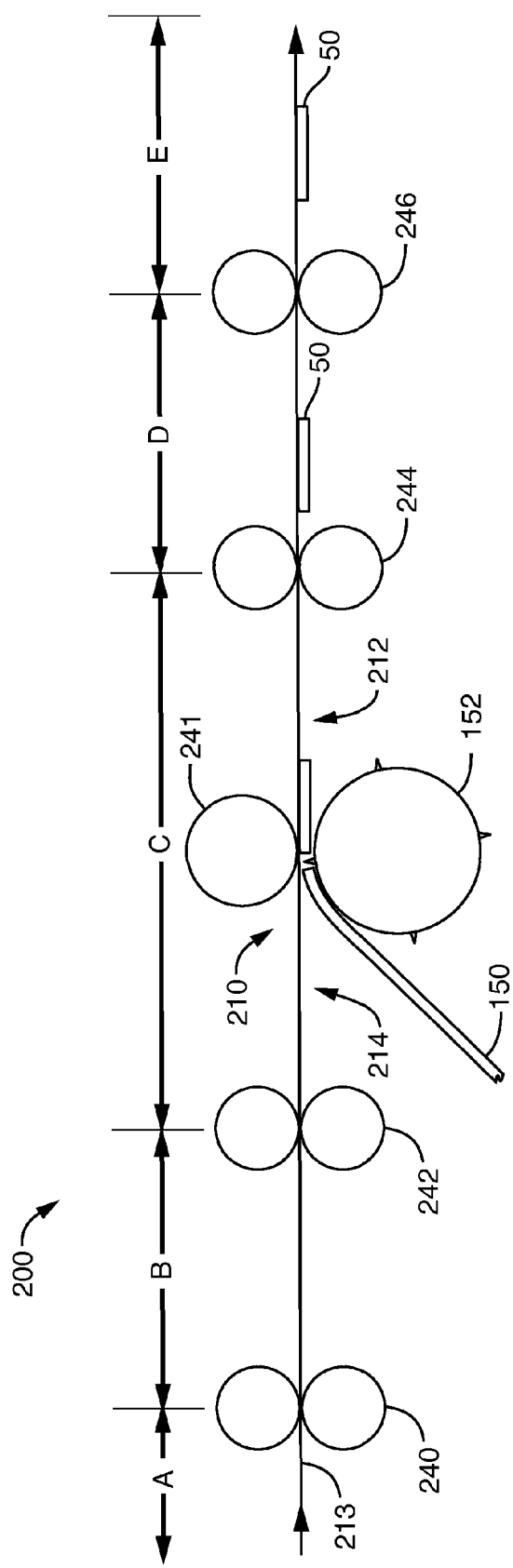
FIG. 7 representatively illustrates a side view of another embodiment of a portion of a garment manufacturing process, the depicted portion incorporating principles of the present invention.

As described earlier, attaching the absorbent assemblies 50 to the continuous web of elastomeric front and back body panel webs 113/117 in a relatively highly stretched state can cause the absorbent assemblies to bunch and gather in use, because upon completion of the manufacturing steps in such an approach, when the front and back body panel webs 113/117 are allow to contract in a finished garment 10, such contraction can cause the absorbent assembly 50 to bunch and gather, which can be undesirable as explained above. Therefore, the present inventors have developed a technique for attaching absorbent assemblies 50 to an elastomeric body panel web (such as one or both of the front body panel web 113 and the back body panel web 117) to assist in reducing or eliminating such bunching or gathering. In the new technique, the region of the elastomeric body panel web to which the absorbent assembly is to be attached is allowed to contract/relax at the time of attachment of the absorbent assembly thereto. In this way, the elastomeric body panel in the finished garment (such as the front body panel 18 and/or the back body panel 20) will impart reduced or no gathering/contracting force upon the absorbent assembly, thus reducing or eliminating unsightly bunching. Specific techniques to cause the elastomeric body panel webs to contract/relax at the point of attachment of the absorbent assembly shall now be described and representatively illustrated in FIGS. 6 and 7. Note that FIGS. 6 and 7 representatively illustrate only a segment of the overall pant manufacturing process 100—namely, the segment indicated by the bracket 200 in FIG. 5, within which the absorbent assemblies 50 are attached to the front body panel web 113 and the back body panel web 117. FIGS. 6 and 7 both illustrate suitable techniques for attaching absorbent assemblies to an elastomeric body panel web; the illustrated techniques are equally suitable for attaching absorbent assemblies to a front body panel web, a back body panel web, a single "full product length" body panel web (as opposed to separate front and back body panel webs), or other similar elastomeric web. (FIGS. 6 and 7 provide additional details regarding certain aspects of the invention which are not presented in FIG. 5.)

Referring to FIGS. 6 and 7, the process 200 comprises stretching one or more elastomeric body panel webs 213 (which could be, for example, a front body panel web 113 or a back body panel web 117). For example, in particular embodiments, the process includes providing first and second elastomeric body panel webs 113/117 both in a stretched state. As used herein, "stretched" means stretched by at least 25% over an unstretched, relaxed length. In certain embodiments, the stretched state constitutes a length which is at least 50%, and preferably at least 100%, greater than an unstretched, relaxed length. In particular embodiments, as noted earlier, the elastomeric body panel web 213 comprises an elastomeric film laminate, such as one in which an elastomeric film layer is sandwiched between opposing nonwoven layers.

The process 200 further comprises contracting the body panel web 213 to define a contracted portion 210. For example, in particular embodiments, the process 200 includes allowing the elastomeric body panel web 213 (such as front panel web 113 and/or back panel web 117) to at least partially contract from the stretched state to a contracted state, thereby defining a contracted portion 210 in the web 213. In certain embodiments, the contracted state can constitute a contraction of at least 50% from the stretched state. In other embodiments, the contracted state can constitute a contraction of at least 75%, of at least 90%, or of 100% from the stretched state.

The process 200 further includes attaching an absorbent assembly 50 to the contracted portion 210 of the elastomeric body panel web 213. For example, as representatively illustrated in FIGS. 6 and 7, a supply of absorbent assemblies 150 may be provided, from which individual absorbent assemblies 50 are cut (and rotated if necessary) and then attached to the contracted portion 210 of each body panel web 213. In particular embodiments, the process 200 further comprises re-stretching at least a portion of the contracted portion 210 of the body panel web 213. For example, the regions of the body panel web 213 immediately leading (region 212) and immediately trailing (region 214) the absorbent assembly 50 can be re-stretched partially or entirely from the contracted state after attachment of the absorbent assembly 50.

In particular embodiments, contracting the body panel web 213 comprise slowing the speed of the body panel web by temporarily securing the body panel web 213 to a first variable-speed member 220. For example, temporarily securing the body panel web 213 to the first variable-speed member occurs via a vacuum force. In other examples, temporarily securing the body panel web 213 to the first variable-speed member occurs via shear frictional forces, such as via a textured surface on the variable-speed member, or via the use of mechanical hook- or mushroom-style fasteners affixed to the variable-speed member and adapted to engage the elastomeric body panel web 213. In one preferable embodiment, the variable-speed member(s) comprise vacuum pucks or plates. Vacuum pucks or plates (pucks or plates having orifices through which a vacuum force flows in order to retain a material thereagainst) are known in the art of personal care manufacture, such as for securely holding absorbent assemblies during attachment to a composite diaper web or sausage.

In one preferable example, the process 200 includes securing the body panel web 213 to a first variable-speed member 220 and to a second variable-speed member 222 spaced from the first variable-speed member. For example, a series of variable-speed members (such as vacuum pucks) may be positioned on the outer surface of a cylindrical drum, or otherwise oriented in a circular pattern such that they rotate about an axis 225 in orbital fashion. In the example depicted in FIG. 6, the variable-speed members are rotating about an axis 225 in a counterclockwise direction. In FIG. 6, a first set of variable-speed members 220/221/222 is shown generally at the top of the rotating circular pattern (with a relative maximum circumferential spacing between them at this point, as shall be explained), while a second set of variable-speed members 220/221/222 is shown generally at the bottom of the rotating circular pattern (with a relative minimum circumferential spacing between them at this point, as shall be explained).

The web 213 is first attached to the variable-speed members 220 and 222 in the radial region generally indicated by the letter A. In region A, the circumferential spacing between the variable-speed members is at its greatest. Next, the first variable-speed member 220 moves circumferentially closer to the second variable-speed member 222 (in the region generally indicated by the letter B), such that the body panel web 213 contracts in a region 211 between the first and second variable-speed members 220/222 to define the contracted portion 210. In the region generally indicated by the letter C, the circumferential spacing between the first and second variable-speed members 220/222 is generally at its least. At this stage, the absorbent assembly 50 is attached to the contracted portion 210 of the body panel web 213. A variable-speed support member 221 (e.g., a moving dead plate) may be positioned radially inward of (i.e., in back of) the web 213 to provide an anvil against which the absorbent assembly 50 may be indirectly pressed to aid in secure attachment of the absorbent assembly 50 to the web 213. Note that in particular embodiments, the variable-speed support member 221 remains substantially unadhered to the web 213. In this way, the web 213 can more easily contract to define the contracted portion 210.

After the absorbent assembly 50 has been attached to the contracted portion 210 of the elastomeric web 213, the first variable-speed member 220 is moved circumferentially away from the second variable-speed member 222. This stage, which occurs in the radial region generally indicated by the letter D, increases the overall speed of the web 213, as certain regions of the web 213 are again stretched. In region D, the body panel web 213 is released from the first and second variable-speed members 220/222, and the overall process 100 continues on as representatively illustrated in the exemplary embodiment of FIG. 5. Note that after the body panel web 213 is released from the first and second variable-speed members 220/222, it is possible in certain embodiments that the overall speed of the web 213 may be (but need not be) slightly slower than the speed of the web prior to entering process 200; this may result from the fact that at least part of the web 213 may now be unstretchably contracted, because at least part of the contracted portion 210 may now be locked or fixed at the relatively shorter contracted distance if such part is affixed to an absorbent assembly which is relatively inextensible.

The embodiment just described and illustrated in FIG. 6 depicts variable-speed members that move in orbital motion about an axis. However, other configurations employing variable-speed members or pucks are possible, such as configurations in which the variable-speed members are positioned in a linear arrangement, such as in conjunction with belts or conveyors.

In another desirable embodiment of the process 200, versions of which are representatively illustrated in FIG. 7, contracting the body panel web 213 comprises slowing the speed of the body panel web 213 using at least one reduced-speed paired-roller nip. Paired-roller nips are known in the industry as means for advancing continuous web-like materials. In one embodiment, such as that depicted in FIG. 7, the process 200 further comprises feeding the body panel web 213 sequentially through a first paired-roller nip 240, a second paired-roller nip 242, a third paired-roller nip 244, and a fourth paired-roller nip 246. In the region generally indicated by the letter A in FIG. 7, the web 213 is in a stretched state. Both the second paired-roller nip 242 and the third paired-roller nip 244 draw more slowly than the first paired-roller nip 244. The consequence of such an arrangement is that the elastomeric body panel web 213 begins to contract in the region generally indicated by the letter B. (In certain embodiments, the second paired-roller nip 242 and the third paired-roller hip 244 draw at substantially the same speed, meaning that their respective draw speeds are not more than 10% different.)

Still referring to FIG. 7, in the region generally indicated by the letter C, the elastomeric web 213 is at the peak of its partially or fully contracted state, and defines a contracted portion 210. The absorbent assembly 50 is attached to the body panel web 213 upon the contracted portion 210, between the second paired-roller nip 242 and the third paired-roller nip 244. In particular embodiments, an anvil or back-up roll 241 is provided opposite the absorbent assembly attachment station or roll 152 to assist in securing attaching each absorbent assembly to the web 213. In this embodiment, the fourth paired-roller nip 246 draws more quickly than the third paired-roller nip 244. The consequence of such an arrangement is that the elastomeric body panel web 213 begins to speed up in the region generally indicated by the letter D. In region D, the regions of the body panel web 213 immediately leading (region 212) and immediately trailing (region 214) the absorbent assembly 50 may in certain embodiments be re-stretched partially or entirely from the contracted state after attachment of the absorbent assembly 50. In the region generally indicated by the letter E, the body panel web 213, after exiting the fourth paired-roller nip 246, continues on in the overall process 100 as representatively illustrated in the exemplary embodiment of FIG. 5. Note that after the body panel web has been contracted, and ultimately exits the fourth paired-roller nip 246, it is possible in certain embodiments that the overall speed of the web 213 may be (but need not be) slightly slower than the speed of the web prior to entering the process 200; this may result from the fact that at least part of the web 213 may now be unstretchably contracted, because at least part of the contracted portion 210 may now be locked or fixed at the relatively shorter contracted distance if such part is affixed to an absorbent assembly which is relatively inextensible.

In an embodiment of the process 200 similar to the one just described and representatively illustrated in FIG. 7, the body panel web 213 first passes through the first paired-roller nip 240. Next, the body panel web passes through the second paired-roller nip 242 downstream of the first paired-roller nip 240. The second paired roller nip 242 has a slower draw than the first paired-roller nip 240. Next, the body panel web 213 passes through a third-paired roller nip 244 downstream of the second paired-roller nip 242. The third paired-roller nip 244 has a draw speed substantially equal to (that is, not more than 10% different than) the draw speed of the second paired-roller nip 242. In one embodiment, the third paired-roller nip 244 has a draw speed identical to the draw speed of the second paired-roller nip 242. Next, the body panel web 213 pass through the fourth paired-roller nip 246 downstream of the third paired-roller nip 244. The fourth paired-roller nip 246 has a faster draw than the third paired-roller nip 244. The absorbent assembly 50 is attached to the body panel web 213 between the second paired-roller nip 242 and the third paired-roller nip 244.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A process for manufacturing disposable absorbent garments, the process comprising:
   stretching an elastomeric body panel web, wherein the body panel web comprises an elastomeric film laminate in which an elastomeric film layer is sandwiched between opposing nonwoven layers;
   thereafter contracting the body panel web to define a contracted portion; and
   attaching an absorbent assembly to the contracted portion of the body panel web.

2. The process of claim 1 further comprising restretching at least a portion of the contracted portion of the body panel web after attaching the absorbent assembly to the contracted portion of the body panel web.

3. The process of claim 1 wherein contracting the body panel web comprises slowing the speed of the body panel web by temporarily securing the body panel web to a first variable-speed member.

4. The process of claim 3 wherein temporarily securing the body panel web to the first variable-speed member occurs via vacuum force.

5. The process of claim 3 further comprising:
   securing the body panel web to the first variable-speed member and to a second variable-speed member spaced from the first variable-speed member;
   moving the first variable-speed member closer to the second variable-speed member, such that the body panel web contracts in a region between the first and second variable-speed members to define the contracted portion;
   after attaching the absorbent assembly to the contracted portion, moving the first variable-speed member away from the second variable-speed member; and
   releasing the body panel web from the first and second variable-speed members.

6. The process of claim 5 wherein the variable-speed members move in orbital motion about an axis.

7. The process of claim 1 wherein contracting the body panel web comprises slowing the speed of the body panel web using a reduced-speed paired-roller nip.

8. The process of claim 7, further comprising feeding the body panel web sequentially through a first paired-roller nip, a second paired-roller nip, a third paired-roller nip, and a fourth paired-roller nip, wherein both the second paired-roller nip and the third paired-roller nip draw more slowly than the first paired-roller nip, wherein the absorbent assembly is attached to the body panel web between the second paired-roller nip and the third paired-roller nip, and wherein the fourth paired-roller nip draws more quickly than the third paired-roller nip.

9. The process of claim 8 further comprising:
passing the body panel web through a first paired-roller nip;
passing the body panel web through a second paired-roller nip downstream of the first paired-roller nip, the second paired-roller nip having a slower draw than the first paired-roller nip;
passing the body panel web through a third paired-roller nip downstream of the second paired-roller nip, the third paired-roller nip having a draw speed substantially equal to the draw speed of the second paired-roller nip;
passing the body panel web through a fourth paired-roller nip downstream of the third paired-roller nip, the fourth paired-roller nip having a faster draw than the third paired-roller nip; and
attaching the absorbent assembly to the body panel web between the second paired-roller nip and the third paired-roller nip.

10. A process for manufacturing disposable absorbent garments, the process comprising:
providing first and second elastomeric body panel webs both in a stretched state, wherein each body panel web comprises an elastomeric film laminate in which an elastomeric film layer is sandwiched between opposing nonwoven layers;
allowing each body panel web to at least partially contract from the stretched state to a contracted state, thereby defining a contracted portion in each body panel web; and
attaching an absorbent assembly to the contracted portion of each body panel web.

11. The process of claim 10 further comprising restretching at least a portion of the contracted portion of the first body panel web.

12. The process of claim 10 wherein contracting the first body panel web comprises slowing the speed of the first body panel web by temporarily securing the first body panel web to a first variable-speed member, and wherein contracting the second body panel web comprises slowing the speed of the second body panel web by temporarily securing the second body panel web to a third variable-speed member.

13. The process of claim 12 wherein temporarily securing the body panel webs to the first and third variable-speed members occurs via vacuum force.

14. The process of claim 12 further comprising:
securing the first body panel web to the first variable-speed member and to a second variable-speed member spaced from the first variable-speed member;
moving the first variable-speed member closer to the second variable-speed member, such that the first body panel web contracts in a region between the first and second variable-speed members to define the contracted portion in the first body panel web;
after attaching the absorbent assembly to the contracted portion in the first body panel web, moving the first variable-speed member away from the second variable-speed member; and
releasing the first body panel web from the first and second variable-speed members;
the process further comprising:
securing the second body panel web to the third variable-speed member and to a fourth variable-speed member spaced from the third variable-speed member;
moving the third variable-speed member closer to the fourth variable-speed member, such that the second body panel web contracts in a region between the third and fourth variable-speedmembers to define the contracted portion in the second body panel web;
after attaching the absorbent assembly to the contracted portion in the second body panel web, moving the third variable-speed member away from the fourth variable-speed member; and
releasing the second body panel web from the third and fourth variable-speed members.

15. The process of claim 14 wherein the first variable-speed member is integral with the third variable-speed member, and wherein the second variable-speed member is integral with the fourth variable-speed member.

16. The process of claim 10, wherein contracting each body panel web comprises slowing the speed of each body panel web using a reduced-speed paired-roller nip.

17. The process of claim 16 further comprising feeding each body panel web sequentially through a first paired-roller nip, a second paired-roller nip, a third paired-roller nip, and a fourth paired-roller nip, wherein both the second paired-roller nip and the third paired-roller nip draw more slowly than the respective first paired-roller nip, wherein the absorbent assembly is attached to each body panel web between the respective second paired-roller nip and the respective third paired-roller nip, and wherein each fourth paired-roller nip draws more quickly than the respective third paired-roller nip.

18. The process of claim 16 further comprising:
passing each body panel web through a first paired-roller nip;
passing each body panel web through a second paired-roller nip downstream of the first paired-roller nip, the second paired-roller nip having a slower draw than the first paired-roller nip;
passing each body panel web through a third paired-roller nip downstream of the second paired-roller nip, the third paired-roller nip having a draw speed substantially equal to the draw speed of the second paired-roller nip;
passing each body panel web through a fourth paired-roller nip downstream of the third paired-roller nip, the fourth paired-roller nip having a faster draw than the third paired-roller nip; and
attaching the absorbent assembly to each body panel web between the second paired-roller nip and the third paired-roller nip.

19. The process of claim 18 wherein the first body panel web passes through a first set of first, second, third, and fourth paired-roller nips, and wherein the second body panel web passes through a second set of first, second, third, and fourth paired-roller nips physically distinct from the first set.

20. A process for manufacturing disposable absorbent garments, the process comprising the steps of:
providing an elastomeric film laminate body panel web traveling at a first production speed;
slowing the travel of the body panel web to an application speed;
providing an absorbent assembly traveling at the application speed;
attaching the absorbent assembly to the body panel web at the application speed; and
accelerating the travel of the body panel web to a second production speed after the absorbent assembly has been attached to the body panel web.

21. The process of claim 20 wherein the second production speed is between 70 and 95 percent of the first production speed.

\* \* \* \* \*